US009534247B2

(12) United States Patent
Park et al.

(10) Patent No.: US 9,534,247 B2
(45) Date of Patent: Jan. 3, 2017

(54) METHOD FOR COLLECTING A SAMPLE OF MICROORGANISMS FROM THE SURFACE OF A SOLID MATERIAL USING A CONTACTLESS PARTITIONING SYSTEM, AND APPARATUS FOR PARTITIONING THE SURFACE OF THE SOLID MATERIAL

(71) Applicant: Sanigen Co., Ltd., Gwacheon, Gyeonggi-Do (KR)

(72) Inventors: Jeong Woong Park, Gyeonggi-Do (KR); Dong Jin Woo, Gyeonggi-Do (KR); Seong Bin Im, Gyeonggi-Do (KR); Sang Woo Kim, Seoul (KR)

(73) Assignee: Sanigen Co., Ltd., Gwacheon, Gyeonggi-do (KR)

( * ) Notice: Subject to any disclaimer, the term of this patent is extended or adjusted under 35 U.S.C. 154(b) by 212 days.

(21) Appl. No.: 13/927,941

(22) Filed: Jun. 26, 2013

(65) Prior Publication Data
US 2013/0288291 A1 Oct. 31, 2013

Related U.S. Application Data

(63) Continuation of application No. PCT/KR2011/010171, filed on Dec. 27, 2011.

(30) Foreign Application Priority Data

Dec. 28, 2010 (KR) .................. 10-2010-0136255
Dec. 27, 2011 (KR) .................. 10-2011-0143022

(51) Int. Cl.
*C12Q 1/24* (2006.01)
*G01N 1/02* (2006.01)
*G02B 27/18* (2006.01)
*G03F 7/20* (2006.01)
*G09F 19/18* (2006.01)

(52) U.S. Cl.
CPC ........ *C12Q 1/24* (2013.01); *G01N 1/02* (2013.01); *G02B 27/18* (2013.01); *G03F 7/70216* (2013.01); *G09F 19/18* (2013.01); *G01N 2001/028* (2013.01)

(58) Field of Classification Search
None
See application file for complete search history.

(56) References Cited

U.S. PATENT DOCUMENTS

| 5,373,748 | A | 12/1994 | Lioy et al. |
| 5,493,400 | A | 2/1996 | Grobler et al. |
| 6,191,850 | B1 | 2/2001 | Chiang |
| 6,357,893 | B1 * | 3/2002 | Belliveau ............... 362/285 |
| 6,397,690 | B1 | 6/2002 | Schroder et al. |
| 2002/0009275 | A1 | 1/2002 | Williams et al. |
| 2007/0072168 | A1 | 3/2007 | Ryle |
| 2008/0278946 | A1 | 11/2008 | Tarter et al. |

FOREIGN PATENT DOCUMENTS

| KR | 1020040102695 | 12/2004 |
| KR | 100947646 B1 | 4/2010 |
| WO | WO-2005/087547 | 8/2006 |
| WO | WO-2008091639 A2 | 7/2008 |

OTHER PUBLICATIONS

Gill et al. "Comparison of methods for sampling and enumerating *Escherichia coli* on pig carcasses". Food Microbiology, 1998, 15, 617-623. ).*
Gill et al. "Assessment of the hygienic characteristics of a beef carcass dressing process". Journal of Food Protection, 1996, vol. 59, No. 2, pp. 136-140.*
Gill, C.O. and Jones, T. "Comparison of methods for sampling and enumerating *Escherichia coli* on pig carcasses", Food Microbiology, 15, pp. 617-623, 1998
Gill, C.O. McGinnis, J.C. and Badoni, M. "Assessment of the Hygenic Characteristics of a Beef Carcass Dressing Process", J. Food Protection, 56(2), pp. 136-140, Feb. 1996 (Feb. 1996).

* cited by examiner

*Primary Examiner* — Vera Afremova
(74) *Attorney, Agent, or Firm* — Mintz Levin Cohn Ferris Glovsky and Popeo, P.C.; Kongsik Kim; Richard B. Emmons

(57) ABSTRACT

The present invention relates to an apparatus for partitioning a sampling region on a solid surface and a method for collecting a microbial sample from a solid surface, in which an optimal sampling region is partitioned on a solid surface using a light source without bringing the solid surface into direct contact with a ruler or a partitioning tool. With the apparatus and method, a solid surface can be prevented from being contaminated during partitioning process, accuracy of sampling operation can be increased, partitioning operation can be continuously performed in a simple manner, and cost of sampling operation can be reduced.

3 Claims, 22 Drawing Sheets

METHOD FOR COLLECTING A SAMPLE OF MICROORGANISMS FROM THE SURFACE OF A SOLID MATERIAL USING A CONTACTLESS PARTITIONING SYSTEM, AND APPARATUS FOR PARTITIONING THE SURFACE OF THE SOLID MATERIAL

CROSS-REFERENCE TO RELATED APPLICATIONS

The present application is a continuation of PCT/KR2011/010171 filed Dec. 27, 2011, which claims priority to Korean Application No. 10-2010-0136255 filed Dec. 28, 2010 and Korean Application No. 10-2011-0143022 filed Dec. 27, 2011, which applications are incorporated herein by reference.

TECHNICAL FIELD

The present invention relates to collecting a microbial sample for use in the preparation of a test sample solution provided in the microbial test method of the Korean Food Standards Codex, and more particularly to a method for collecting a microbial sample from a solid surface using a contactless partitioning system and to an apparatus for partitioning a sampling region on a solid surface, wherein the sampling region for microbial analysis is partitioned on the solid surface using a light source without bringing the light source in contact with the solid surface, and thus it is possible to prevent microbial contamination which occurs when the partitioning operation is performed using a template, and the sampling operation can be simplified, resulting in a significant reduction in the sampling time, and furthermore, the partitioning apparatus can be used multiple times, resulting in a reduction in the cost incurred in the sampling operation.

BACKGROUND ART

The Korean Food Sanitation Act provides that the Commissioner of the Korea Food and Drug Administration shall determine and publicly announce standards for manufacturing, processing, cooking or storing foods or food additives, when necessary for public health (Food Standards Codex).

With this Food Standards Codex, Article 7 of the Korean Food Sanitation Act provides standards for manufacturing, processing, using, cooking and storing foods, food additives, devices, containers and packages, and standards for ingredients. In addition, the Korean Food Sanitation Act provides standards and specifications for 20 food groups, 138 food classes and 480 food types, standards and specifications for devices, containers and packages according to 45 kinds of materials, and testing methods therefor.

The Korean Food Standards Codex was provided based on the Korean Food Sanitation Act established on Jan. 20, 1962 and was first opened in the year 1966 by announcing standards and specifications for alcoholic beverages and soy source.

Since then, the management system of the Korean Food Standards Codex was established in Dec. 23, 1967 by announcing standards for the manufacture, processing and use of soy source and provisions for the ingredients thereof under Decree No. 206 of the Ministry of Health and Social Affairs. In the year 1976, the Korean Food Sanitation Act was amended while the standards and specifications determined by the decrees of the Ministry of Health and Social Affairs were changed to those determined by the notices of the Ministry of Health and Social Affairs, and in the year 1977, standards and specifications for foods and the like were wholly amended to provide a basis on which the current Korean Food Sanitation Act is based. Since then, the Korean Food Standards Codex was amended several times, and with the launch of the WTO, it was converted to a management system that loosens quality standards while enforcing safety. With the loosening of quality standards, the desire to develop new products has been boosted. In addition, the Korean Food Standards Codex has been continually amended such that it could be harmonized with international standards.

Moreover, the Korean Food Standards Codex includes general provisions, methods for the collection and handling of samples, common standards and specifications for general foods, standards and specifications for each food, recommended microbial standards for foods to be cooked and marketed by food service establishments, provisional standards for marine products, standards and specifications for devices, containers and packages, general testing methods, reagents, sample solutions, standard solutions, standard solution for volumetric analysis, and appenda.

In the Korean Food Standards Codex, sampling methods are described according to the kind of sample (heterogeneous food, sample for microbial analysis, package sample, fishes and shells, etc.).

Among them, the sampling methods for microbial analysis include various sampling methods for liquid samples, semi-solid samples, solid samples, solid surface samples, and powder samples.

In the sampling methods for solid surface samples, a specific area is partitioned on the solid surface, and a sample is collected from the partitioned area and used as a microbial test solution.

For the solid surface sampling as described above, a region having a specific size should be partitioned on the solid surface. In order to partition a region having specific size on the solid surface, the region having a specific size is partitioned on the solid surface using a ruler and a pen, and the partitioned region is sampled. Alternatively, a separately prepared template is attached to the solid surface, and the region partitioned thereby is sampled. In other words, a plurality of partitioned regions having a constant size are sampled to obtain standards.

However, in the conventional sampling methods as described above, tools, such as a ruler, a pen or a template, are used, and thus there are serious problems in that the tools cause instantaneous microbial contamination when they come into contact with the solid surface, and furthermore, result in the error of microbial sampling.

In recent years, in order to overcome the above-described problems, a template sterilized by gamma radiation has been used. This template can minimize contamination caused by a tool used to partition a sampling region on the solid surface.

The above-described sterilized template can minimize the contamination of the solid surface, because it is used after sterilization. However, it is expensive because it is sterilized. Further, it is disposable and non-recyclable, and thus when several regions of the solid surface are to be sampled, a plurality of the templates should be used, resulting in an increase in analysis cost. In addition to these problems, the template should be attached to each region, making the analysis process very complicated.

SUMMARY OF THE DISCLOSURE

The present invention has been made in order to solve the above-described problems, and it is an object of the present invention to provide a method for collecting a microbial sample from a solid surface using a contactless partitioning system and an apparatus for partitioning a sampling region on a solid surface, in which an optimal sampling region is partitioned on a solid surface using a light source without bringing the solid surface into direct contact with a ruler or a partitioning tool, and thus the solid surface can be prevented from being contaminated during the partitioning process, the accuracy of the sampling operation can be increased, the partitioning operation can be continuously performed in a simple manner so as to reduce the time of the sampling operation, and particularly the apparatus can be used many times, resulting in a reduction in the cost of the sampling operation.

To achieve the above object, the present invention provides A method for collecting a microbial sample from a solid surface using a contactless partitioning method, the method comprising steps of: projecting a figure-shaped partitioned image corresponding to a sampling region onto the solid surface which is contactless with a light from a projecting light source; determining the figure-shaped sampling region projected on the solid surface by controlling the light source; collecting microorganisms from the sampling region by wiping the partitioned sampling region with a collection means; and preparing a suspension of the microorganisms by mixing and strongly shaking the collection means for collecting microorganisms with sterile physiological saline.

The present invention also provides an apparatus for contactlessly partitioning a sampling region on a solid surface, the apparatus comprising: a body; a battery for supplying power included in the body; an operating switch for turning ON/OFF power at the top; a light source at the bottom of the body which downwardly irradiates a light; and a partitioning means for partitioning a figure-shaped sampling region below the light source wherein the light irradiated from the light source through the partitioning means projects an image corresponding to a sampling region onto the solid surface.

When the above-described method for collecting a microbial sample from a solid surface using a contactless partitioning system and the above-described apparatus for partitioning a solid surface are used, a figure-shaped sampling region is projected and partitioned on a solid surface using a light source, and thus an optimal sampling region from which a sample is to be collected can be partitioned on the solid surface. Also, because the contactless method is used, the solid surface can be prevented from being contaminated by the partitioning apparatus, and thus the accuracy of the sampling operation can be increased and the sampling time can be significantly reduced.

In addition, because the apparatus can be used according to the ON/OFF operation of the light source, it can be continuously used several times, and thus the sampling operation cost caused by the use of a partitioning tool can be reduced.

DESCRIPTION OF REFERENCE NUMERALS USED IN THE DRAWINGS

Figure 1:
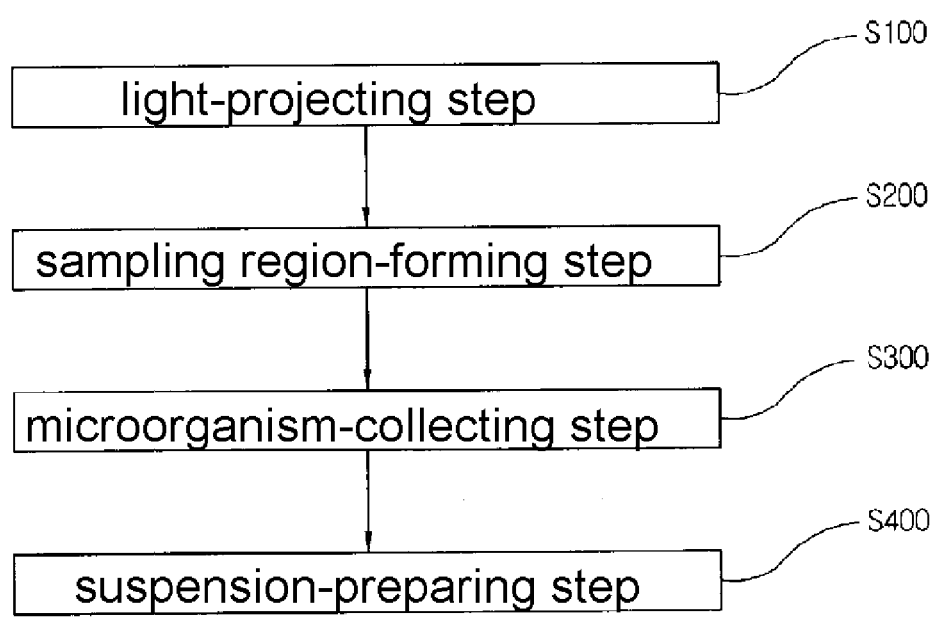
FIG. 1 is a flow chart showing a method for collecting a microbial sample from a solid surface using a contactless partitioning system according to the present invention.

10: sampling region
20: a partitioned image
100: body
110: battery
120: operating switch
130: light source
131 and 131': lamp-type light source
132: main light source
132a: central point
133: auxiliary light source
133a: auxiliary point
135: straight light source
140: partitioning means
141 and 141': colored filter
142: partitioning portion
142a and 142a': partitioning line
142b and 142b': partitioning surface
145: diffraction lens; P: solid surface
S100: light-projecting step
S200: sampling region-forming step
S300: microorganism-collecting step
S400: suspension-preparing step

DETAILED DESCRIPTION

The terms or words used in the specifications and claims should not be limited to be construed as usual or dictionary definition but should be rather construed to be consistent with the technical spirits of the present invention based on the principle that the inventors may properly define the terms used in the specification to describe their invention in the best manner.

Accordingly, it should be understood that the embodiments described in the specification and configurations disclosed in the drawings are merely examples and do not represent all of the technical spirits of the invention and various modifications and variations to the invention and equivalents thereof may be made at the time of the invention.

Hereinafter, preferred embodiments of the inventive method for collecting a microbial sample from a solid surface using a contactless partitioning system will be described in detail with reference to the accompanying drawings.

FIG. 1 is a flow chart showing the inventive method for collecting a microbial sample from a solid surface using a contactless partitioning system.

As shown in FIG. 1, the inventive method for collecting a microbial sample from a solid surface using a contactless partitioning system comprises the sequential steps of: (S100) projecting a partitioned image 20 on a solid surface P using a light source; (S200) controlling the partitioned image 20 to form a sampling region; (S300) collecting microorganisms from the sampling region; and (S400) preparing a suspension of the collected microorganisms.

In the method of the present invention, the partitioned image-projecting step (S100) is performed to project a light source onto the solid surface P in order to form a sampling region 10. The step (S100) is performed by irradiating the solid surface with light from a light source spaced apart from the solid surface and projecting the figure-shaped partitioned image, which corresponds to the sampling region, onto the solid surface (P) using the irradiated light.

Also, the sampling region-forming step (S200) is performed by controlling the light irradiated onto the solid surface (P). Specifically, the distance between the solid surface (P) and the light source is controlled to partition the figure-shaped sampling region 10 corresponding to an area for collecting microorganisms from the solid surface (P).

Also, the microorganism-collecting step (S300) is performed to collect microorganisms from the partitioned sampling region 10. In this step, microorganisms are collected by wiping the sampling region 10 with a collection means. Herein, the collection means that is used to collect microorganisms may be a sterile gauze or cotton swab wetted with 1-5 ml of sterile physiological saline.

In order words, microorganisms present in the sampling region are collected by adsorption using the sterile gauze or cotton swab.

Moreover, the suspension-preparing step (S400) is performed by mixing the collection means, used to collect microorganisms in the microorganism collection step (S300), with sterile physiological saline, and strongly shaking the mixture to prepare a suspension of the collected microorganisms. Specifically, the step (S400) is performed by mixing the collection means such as the sterile gauze or cotton swab with 10-100 ml of sterile physiological saline.

In other words, the process of collecting the microbial sample is performed by mixing the collected microorganisms with sterile physiological saline in a conventional Erlenmeyer flask or test tube (not shown in the drawings) and preparing a suspension of the microorganisms from the mixture using a shake culture method which is applied for cell culture.

Meanwhile, in the sample collection method as described above, the sampling region 10 may have various shapes. In the present invention, a square shape and a circular shape are preferably applied. Hereinafter, preferred embodiments of the present invention will be described in detail with reference to the accompanying drawings.

First, in the step (S100) of projecting light from the light source, light from a two-part lamp-type light source which emits diffused light is passed through a filter to project a linearly partitioned image 20.

In the step (S200) of forming the sampling region, the distance between the light source and the solid surface (P) is controlled, so that a linearly partitioned region having an area corresponding to the sampling region 10 can be formed when the opposite ends of two partitioned images 20 and 20' projected from the light sources first come in contact with each other.

Figure 2:
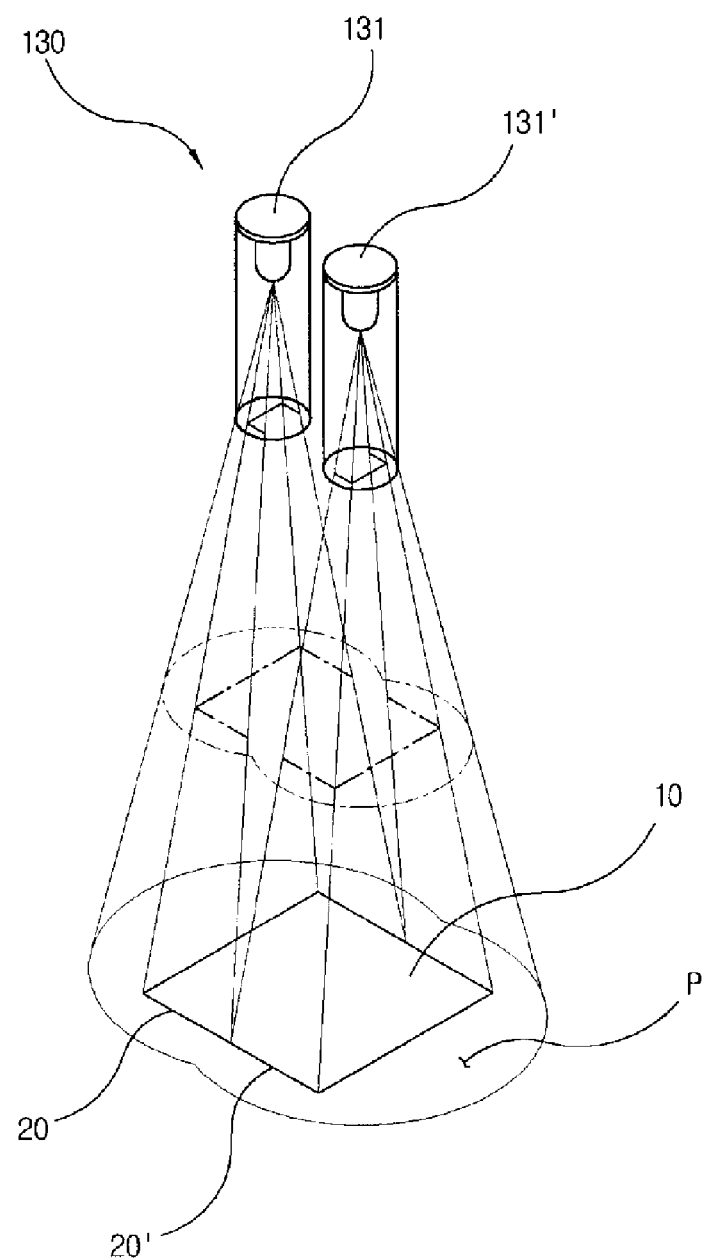
FIG. 2 shows a first embodiment of a sampling region partitioned using a two-part lamp-type light source in a method for collecting a microbial sample from a solid surface using a contactless partitioning system according to the present invention.

In other words, when the sampling region 10 is to be partitioned by a square shape as shown in FIG. 2, the light source on one side (left) may project a partitioned image having a "⌊" shape onto the solid surface P, and the light source on the other side (right) may project a partitioned image 20' having a "⌉" onto the solid surface P.

In the step (S200) of forming the sampling region, the two partitioned images 20 and 20' projected from the light sources are controlled to be enlarged so that a sampling region 10 having a "☐" shape can be formed when the opposite ends of the partitioned images 20 and 20' first come into contact with each other.

Figure 3:
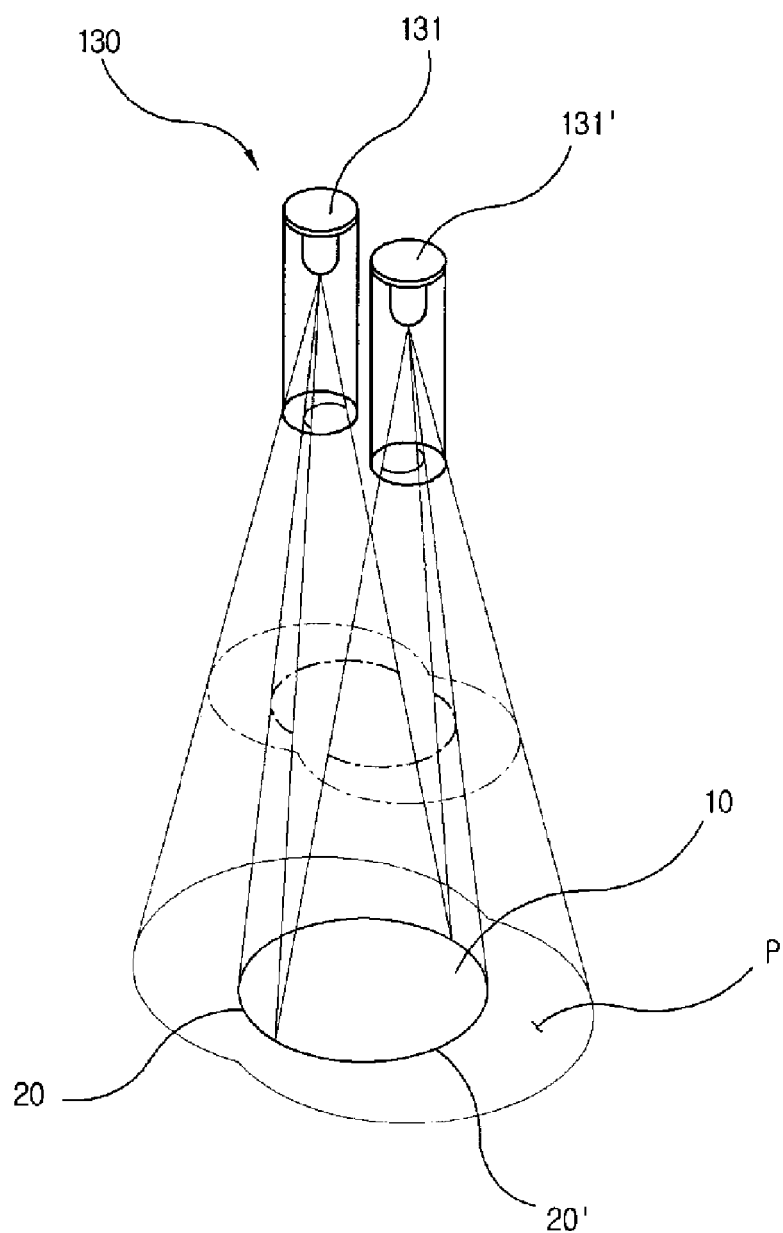
FIG. 3 shows a second embodiment of a sampling region partitioned using a two-part lamp-type light source in a method for collecting a microbial sample from a solid surface using a contactless partitioning system according to the present invention.

Further, when the sampling region 10 is to be partitioned by a circular shape as shown in FIG. 3, the light source on one side (left) may project a partitioned image having a "(" shape onto the solid surface P, and the light source on the other side (light) may project a partitioned image having a ")" shape onto the solid surface P.

In the step (S200) of forming the partitioned region, the two partitioned images 20 and 20' projected from the light sources are controlled to be enlarged, so that a sampling region 10 having a "◯" shape can be formed when the opposite ends of the partitioned images 20 and 20' first come into contact with each other.

In another embodiment, light from a four-part lamp-type light source which emits diffused light is passed through a filter to project linearly partitioned images 20 and 20'.

In the step (S200) of forming the sampling region, the distance between the light source and the solid surface (P) is controlled, so that a linearly partitioned sampling region having an area corresponding to the sampling region 10 can be formed when the opposite ends of the partitioned images 20 and 20' projected from the light sources first come into contact with each other.

Figure 4:
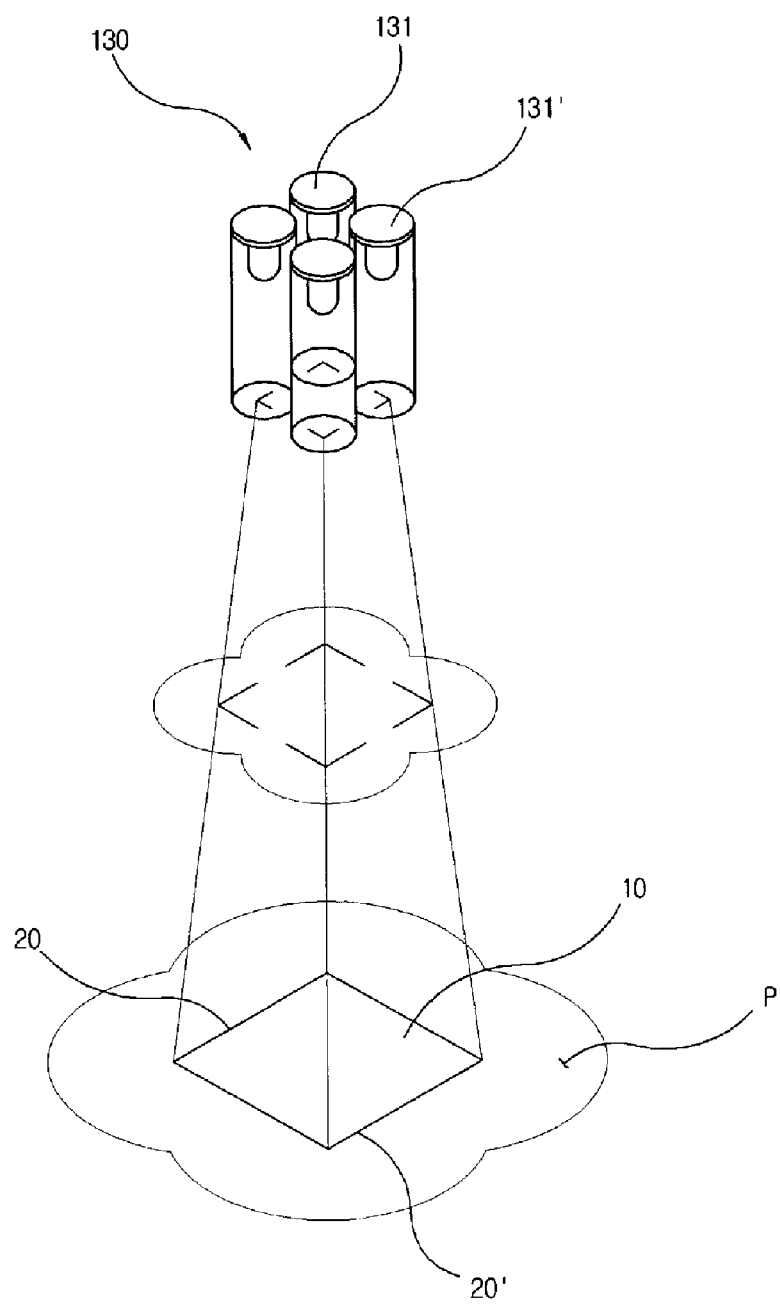
FIG. 4 shows a first embodiment of a sampling region partitioned using a four-part lamp-type light source in a method for collecting a microbial sample from a solid surface using a contactless partitioning method according to the present invention.

Specifically, when the sampling region 10 is to be partitioned by a square shape as shown in FIG. 4, partitioned images 20 and 20' having shapes of "⌊", "⌈", "⌋" and "⌉", respectively, are projected using four radially filtered lamp-type light sources in the step (S100) of projecting light images. In the step (S200) of forming the sampling region, the distance between the four partitioning images 20 and 20' projected from the light sources and the solid surface P is controlled so that a sampling region 10 having a "☐" shape can be partitioned when the ends of the partitioned images 20 and 20' first come into contact with each other.

Figure 5:
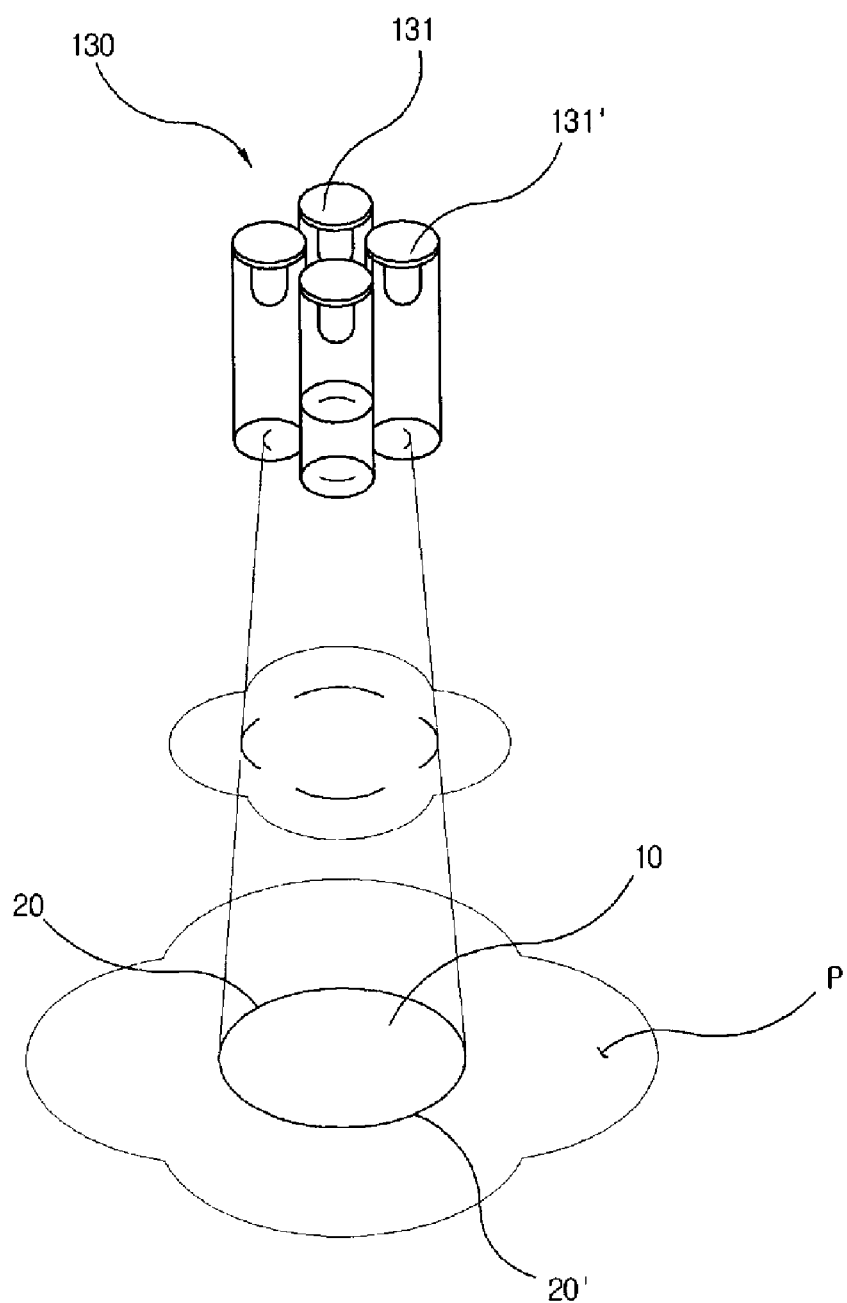
FIG. 5 shows a second embodiment of a sampling region partitioned using a four-part lamp-type light source in a method for collecting a microbial sample from a solid surface using a contactless partitioning method according to the present invention.

Also, when the sampling region 10 is to be partitioned by a circular shape as shown in FIG. 5, partitioning images 20 and 20' having shapes of "\", "⌒", "⌣" and "⌢" are projected four radially filtered lamp-type light sources in the step (S100) of projecting light images. In the step (S200) of forming the sampling region, the distance between the four partitioning images 20 and 20' projected from the light sources and the solid surface P is controlled so that a sampling region 10 having a "◯" shape can be partitioned when the ends of the partitioned images 20 and 20' first come into contact with each other.

In another embodiment, light from a single lamp-type light source is passed through a filter to project a linearly partitioned image 20. In step (S200) of forming the sampling region, the distance between the partitioned image 20 projected from the light source and the solid surface P is controlled so that a linearly partitioned sampling region 10 can be formed by an enlarged image.

Figure 6:
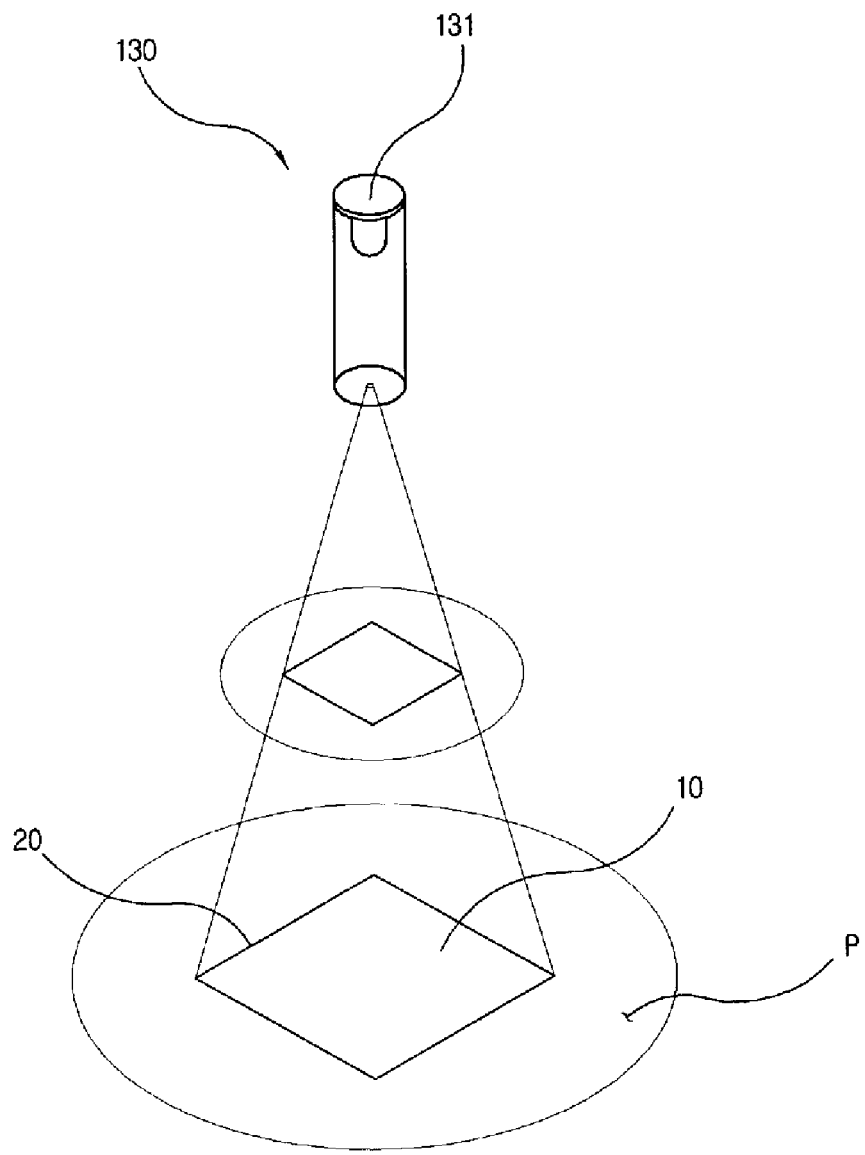
FIG. 6 shows a first embodiment of a sampling region partitioned using a single lamp-type light source in a method for collecting a microbial sample from a solid surface using a contactless partitioning system according to the present invention.
Figure 7:
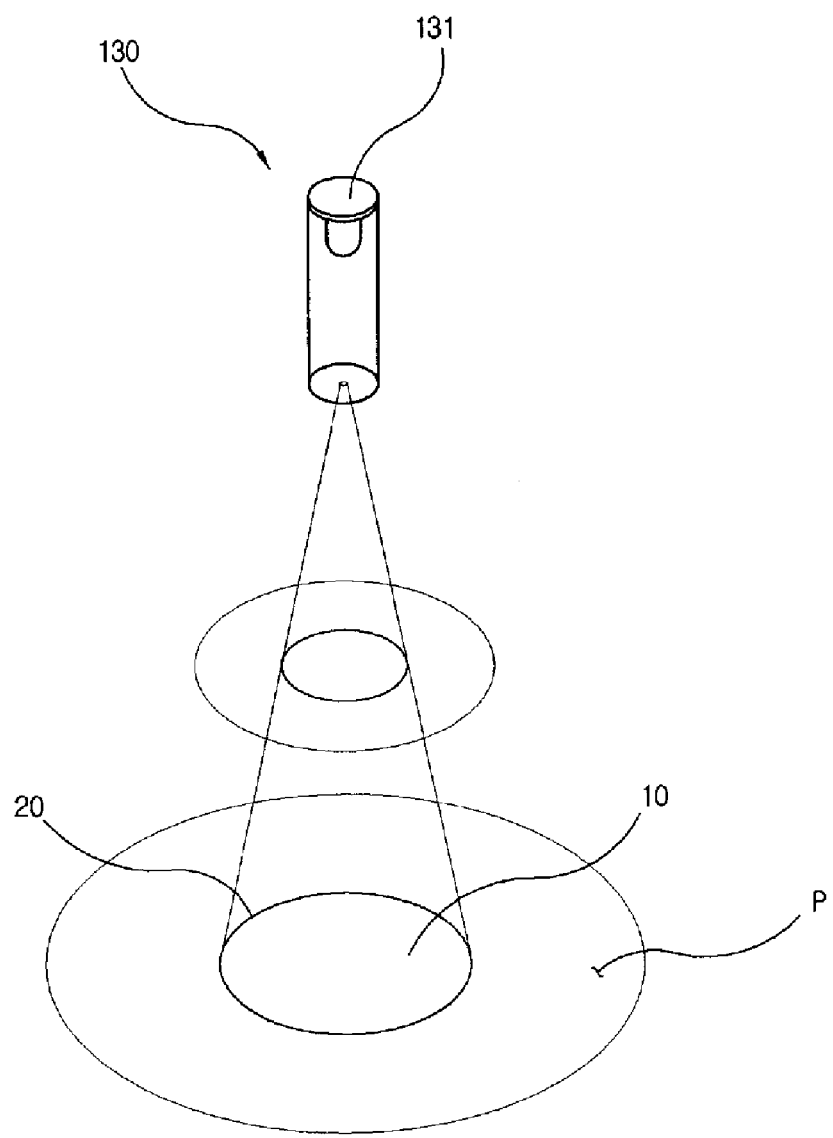
FIG. 7 shows a second embodiment of a sampling region partitioned using a single lamp-type light source in a method for collecting a microbial sample from a solid surface using a contactless partitioning system according to the present invention.

Specifically, as shown in FIGS. 6 and 7, one filtered lamp-type light source is used in the step (S100) of projecting the light source. The light source projects a partitioned image 20 having any one shape of "☐" and "◯" through a filter. In the step (S200) of forming the sampling region, the partitioned image projected from the light source is controlled to be enlarged, so that a sampling region 10 having any one shape of "☐" and "◯" may be formed.

Meanwhile, in the step (S100) of projecting the light source, light from the light source may be passed through a filter to project a partitioned surface image 20.

Figure 8:
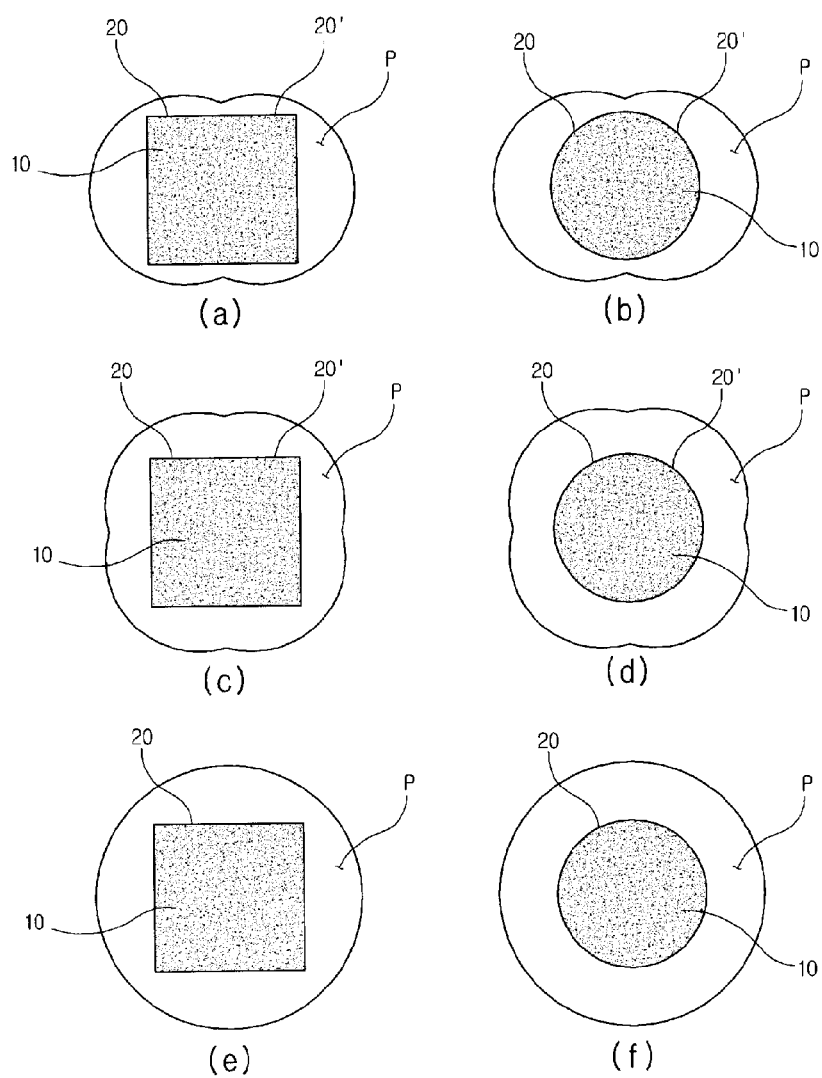
FIG. 8 shows an example of a sampling region partitioned using a single or four-part lamp-type light source in a method for collecting a microbial sample from a solid surface using a contactless partitioning system according to the present invention.

As shown in FIG. 8, in the step (S200) of forming the sampling region, the distance between a partitioning image 20 projected from a light source and the solid surface P is controlled so that a figure-shaped sampling region 10 having any one surface shape of "■" and "●" can be partitioned by the enlarged image.

In addition, a single laser-type main light source having straightness and an auxiliary light source may be used. Herein, the main light source projects a figure-shaped partitioned image 20 having a central point 132a through a diffraction lens that emits diffused light, and the auxiliary light source projects a slant auxiliary point 133a that progresses toward the central point 132a. In the step (S200) of forming the sampling region, the distance between the light sources and the solid surface is controlled so that a linearly partitioned sampling region 10 can be formed when the central point 132a and the auxiliary point 133a overlap each other.

Figure 9:
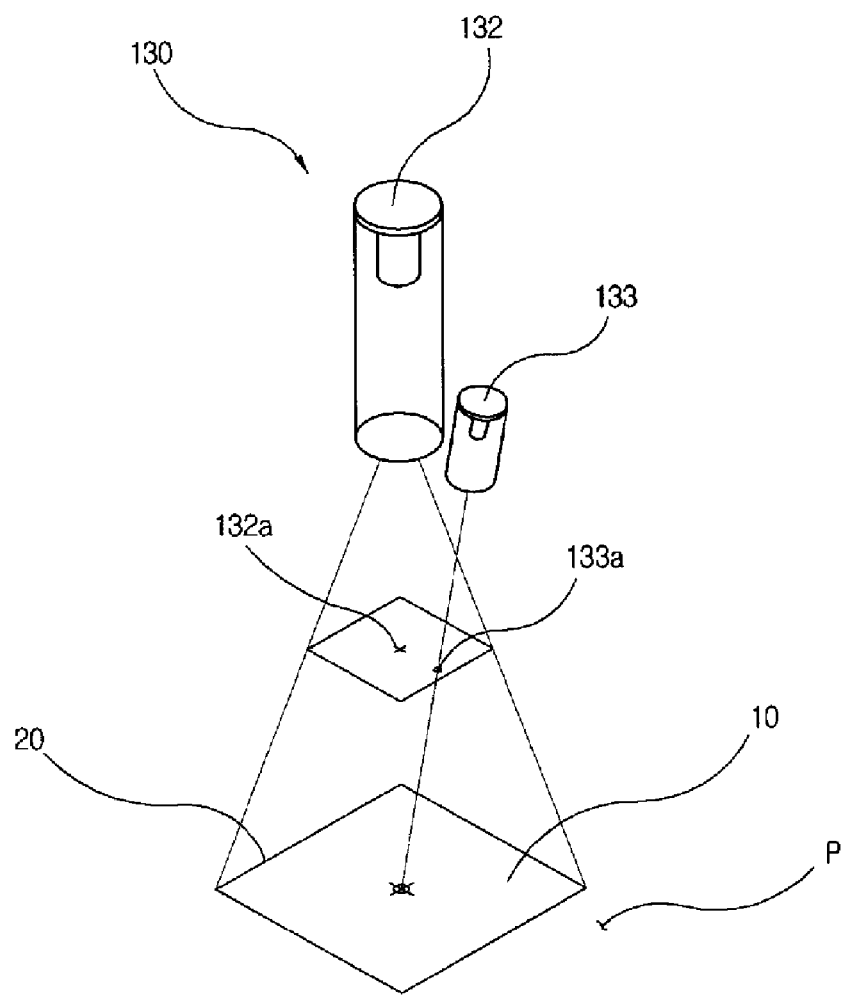
FIG. 9 shows a first embodiment of a sampling region partitioned using a laser-type light source with an auxiliary light source in a method for collecting a microbial sample from a solid surface using a contactless partitioning system according to the present invention.
Figure 10:
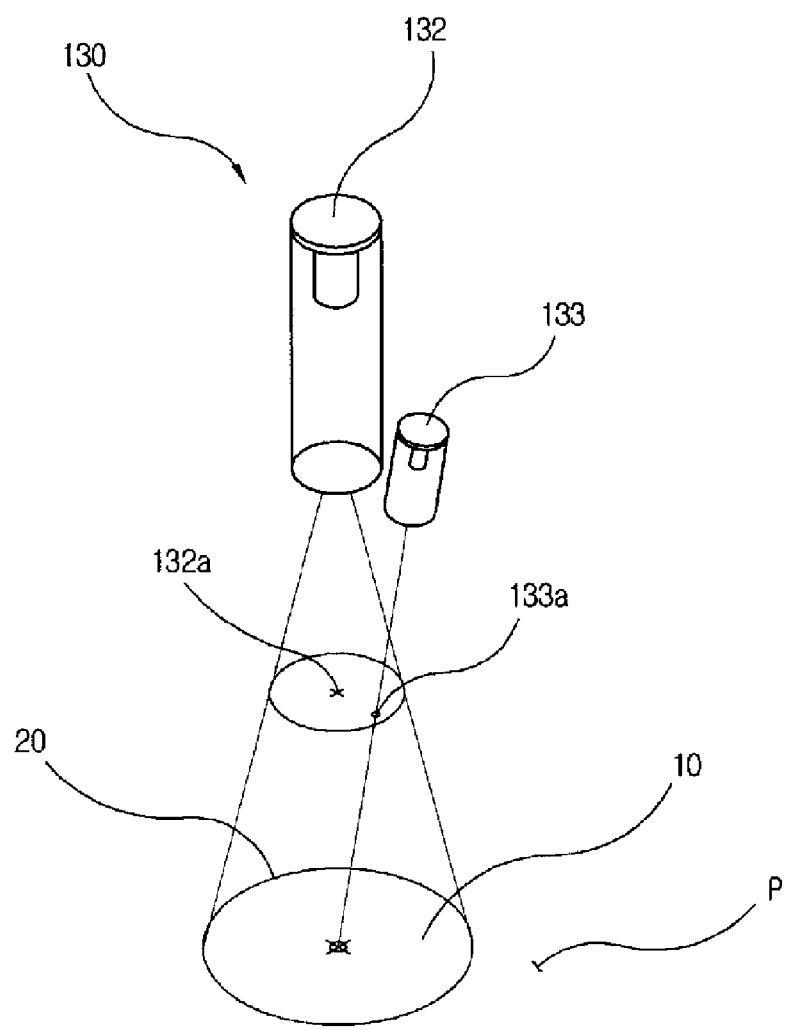
FIG. 10 shows a second embodiment of a sampling region partitioned using a laser-type light source with an auxiliary light source in a method for collecting a microbial sample from a solid surface using a contactless partitioning system according to the present invention.

Specifically, as shown in FIGS. 9 and 10, in the step (S100) of projecting the light source, the main light source projects a partitioning image having a "⊡" or "⊙" shape having a central point 132a through a diffraction lens that emits diffused light, and the auxiliary light source projects a slant auxiliary point 133a that progresses toward the central point 132a. In the step (S200) of forming the sampling region, the levels of the images projected from the main light source and the auxiliary light source are controlled, so that a partitioned sampling region 10 having any one shape of "⊡" and "⊙" when the central point 132a and the auxiliary point 133a overlap each other.

Herein, the above central point and auxiliary point may have various shapes such as "•" or "x".

Figure 11:
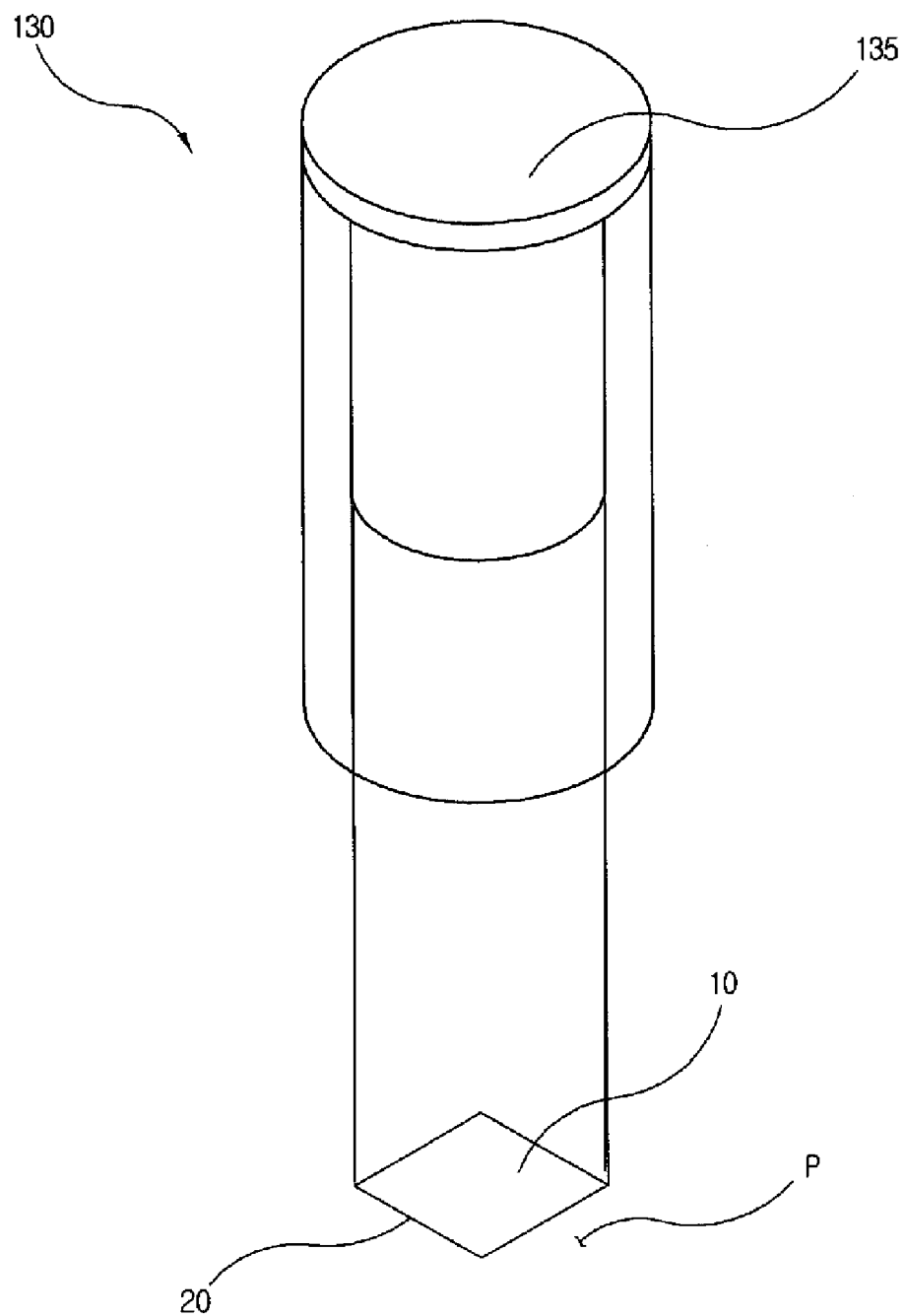
FIG. 11 shows a first embodiment of a sampling region partitioned using a laser-type light source in a method for collecting a microbial sample from a solid surface using a contactless partitioning system according to the present invention.
Figure 12:
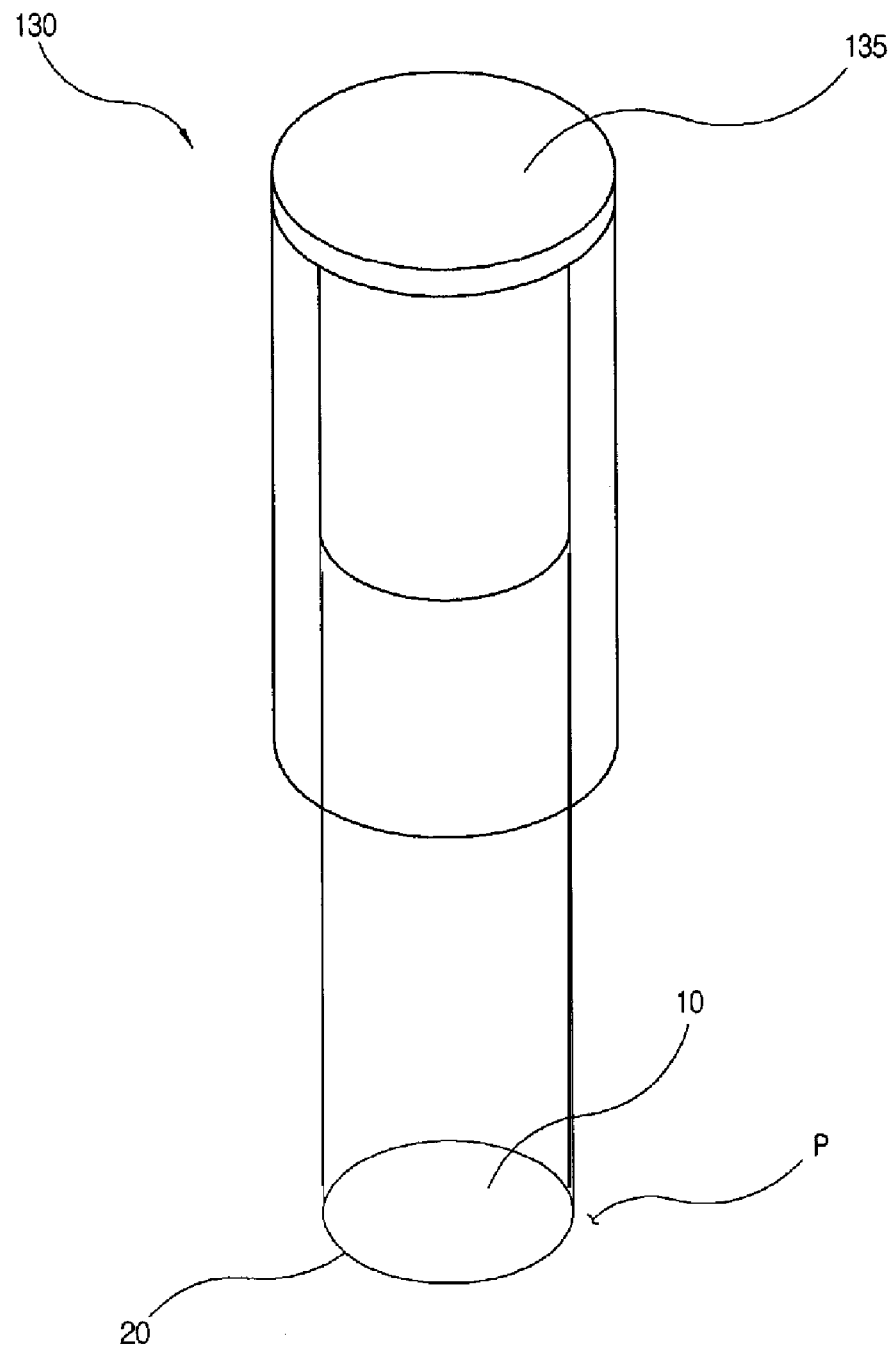
FIG. 12 shows a second embodiment of a sampling region partitioned using a laser-type light source in a method for collecting a microbial sample from a solid surface using a contactless partitioning system according to the present invention.

In addition, using a single laser-type light source having straightness, an image having a predetermined shape is projected from the light source, so that a linearly partitioned sampling region 10 can be formed. Specifically, as shown in FIGS. 11 and 12, an image having any one shape of "☐" and "◯" is projected from the light source, so that a linearly partitioned sampling region 10 can be formed.

Meanwhile, in the step (S200) of forming the sampling region, the partitioned sampling region 10 formed by projecting the image from the light source most preferably has an area of 100 cm².

Hereinafter, an apparatus for partitioning a sampling region on a solid surface in a contactless manner, which is used in the above-described method for collecting a microbial sample from a solid surface using a contactless partitioning system, will be described in detail with reference to the accompanying drawings.

Figure 13:
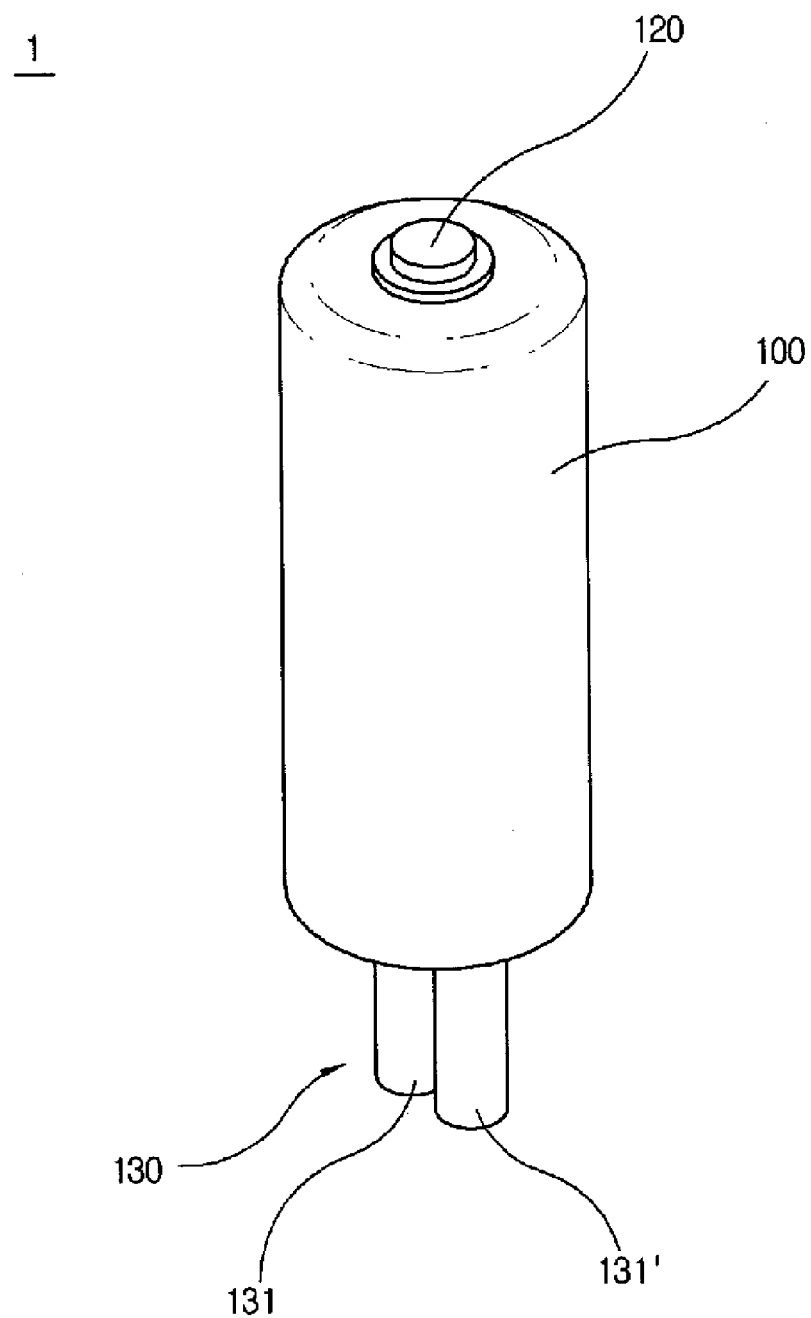
FIG. 13 is a perspective view showing a first embodiment of the inventive apparatus for partitioning a sampling region on a solid surface in a contactless manner.
Figure 14:
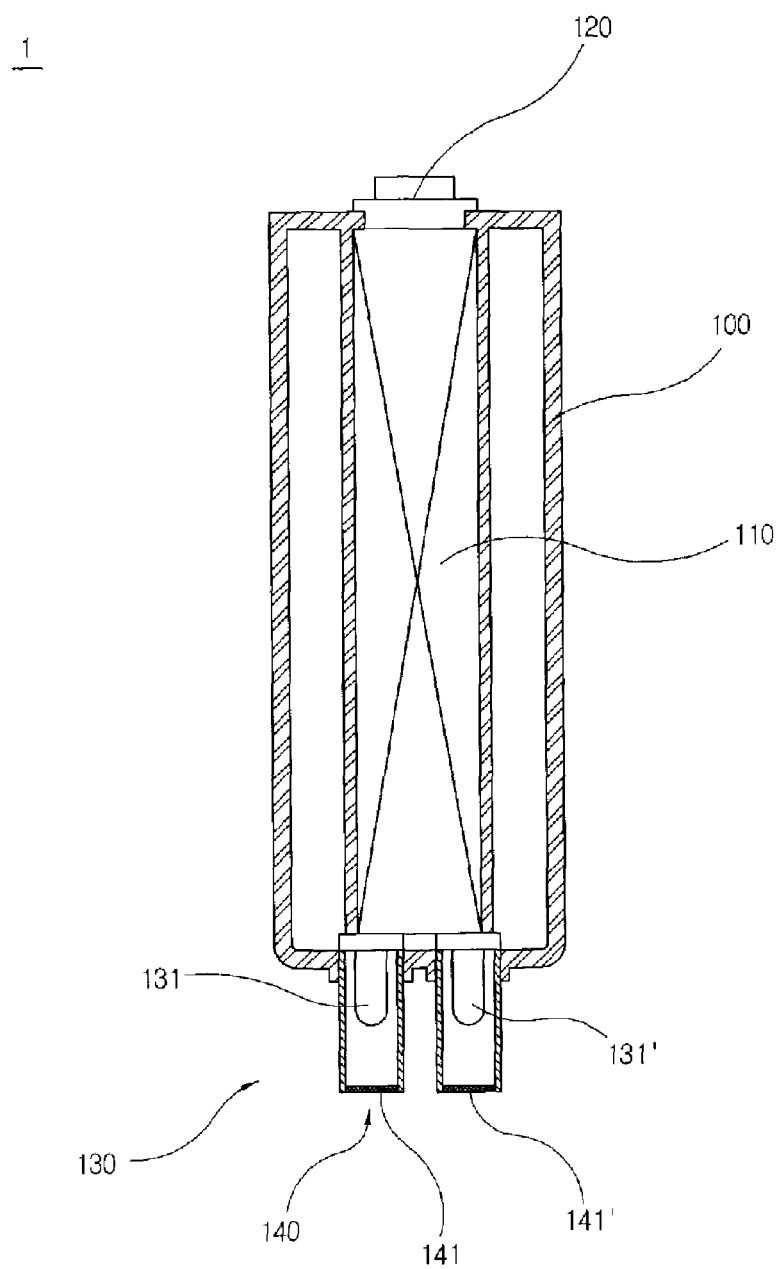
FIG. 14 is a cross-sectional view showing a first embodiment of the inventive apparatus for partitioning a sampling region on a solid surface in a contactless manner.

FIG. 13 is a perspective view showing a first embodiment of the inventive apparatus for partitioning a sampling region on a solid surface in a contactless manner, and FIG. 14 is a cross-sectional view showing a first embodiment of the inventive apparatus for partitioning a sampling region on a solid surface in a contactless manner.

As shown in FIGS. 13 and 14, the inventive apparatus 1 for partitioning a sampling region on a solid surface in a contactless manner comprises a small-sized cylindrical body 100 which is easily grasped by the operator's hand.

Herein, a battery 110 for supplying power is included in the body so that it can be used as a power source. In addition, an ON/OFF operating switch which is electrically connected to the battery 110 is provided at the top of the body 100 so as to be exposed to the outside.

Also, a light source 130 which faces downward is provided at the bottom of the body 100 and is switched ON/OFF by the operation of the operating switch 120.

Further, a partitioning means 140 for partitioning a figure-shaped sampling region 10 is provided below the light source 130 and is configured such that light from the light source 130 passes through the partitioning means 140 so that an image corresponding to the sampling region 10 is projected onto the solid surface P.

Figure 17:
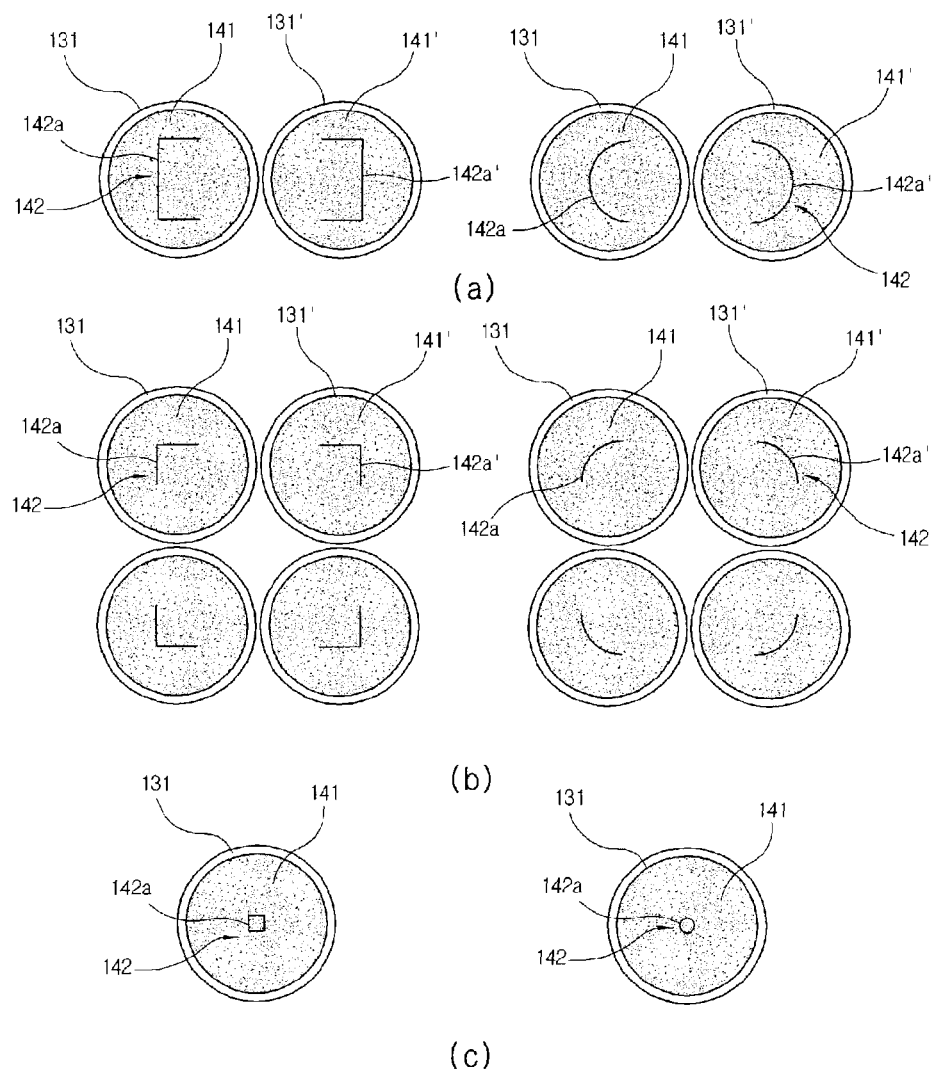
FIG. 17 is a top view showing a first embodiment of a filter in the inventive apparatus for partitioning a sampling region on a solid surface in a contactless manner.
Figure 18:
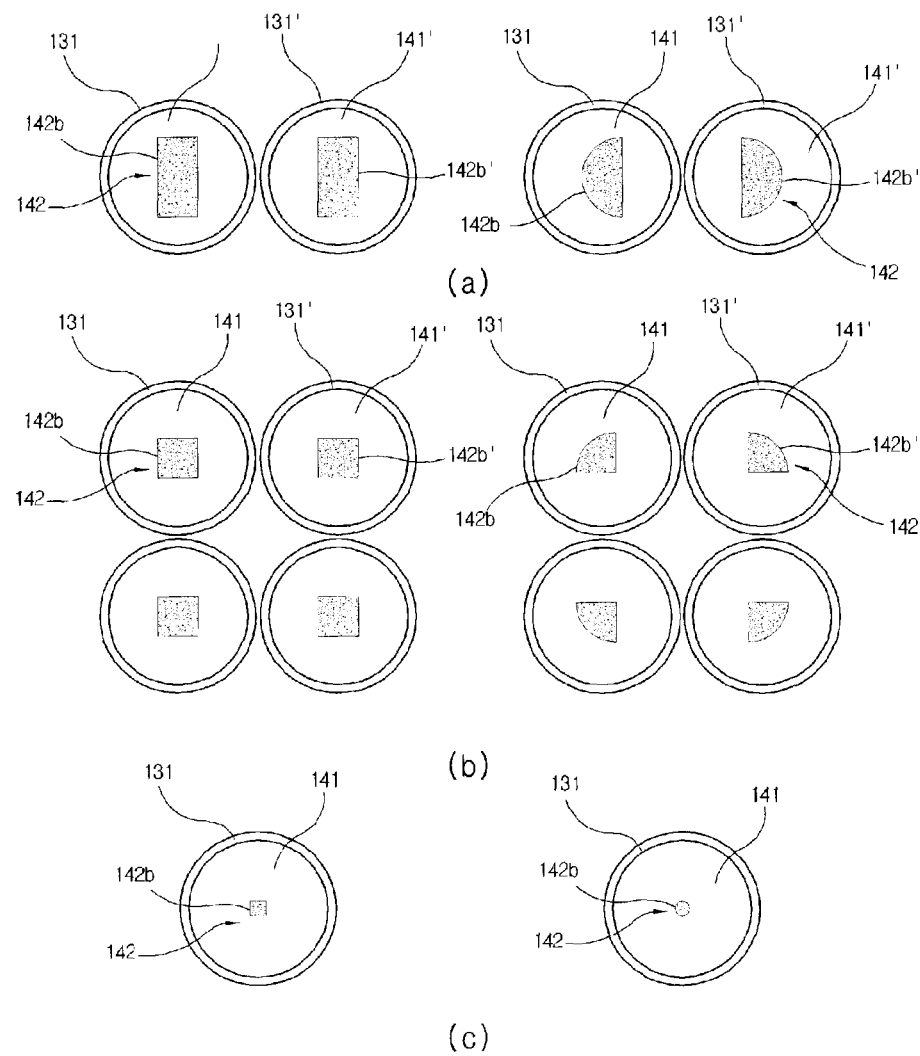
FIG. 18 is a top view showing a second embodiment of a filter in the inventive apparatus for partitioning a sampling region on a solid surface in a contactless manner.

Herein, the light source includes a lamp-type light source that emits diffused light, and the partitioning means 140 includes a colored filter which is generally impermeable to light, provided that a transparent, light-permeable partitioning region is formed in the center of the colored filter 141 as shown in FIGS. 17 and 18, so that light from the light source 130 passes through the partitioning portion 142 of the colored filter 141 to project the figure-shaped sampling region 10 on the solid surface P.

Meanwhile, the sampling region 10 as described above may have various shapes. In the present invention, a square shape and a circular shape are applied. Preferred embodiments of the present invention will be described in detail with reference to the accompanying drawings.

Each of the lamp-type light source and the colored filter 141 is divided onto two parts. As shown in FIG. 17(a), the partitioning portions 142 of the colored filters 141 and 141' include two opposite linear partitioning FIGS. 142a and 142a' having shapes of "[" and "]" or "(" and ")", so that light having passed through each of the colored filters 141 and 141' forms a linearly partitioned sampling region 10 on the solid surface 10.

Specifically, when the sampling region 10 is partitioned on the solid surface P using two lamp-type light sources 131 and 131' and colored filters 141 and 141' as described above, the sampling region 10 having a "☐" or "◯" shape as shown in FIG. 2 or 3 with respect to the sample collection method is partitioned.

Figure 15:
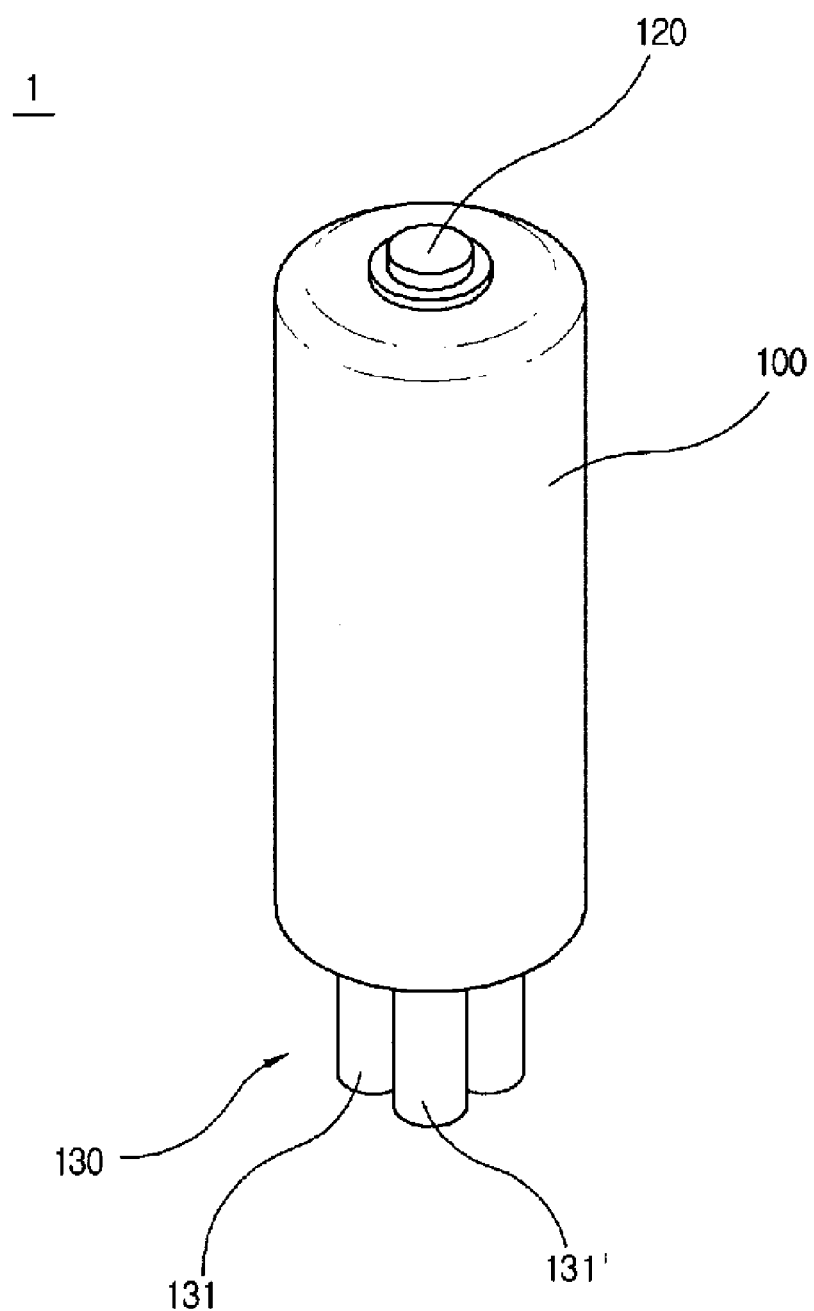
FIG. 15 is a perspective view showing a second embodiment of the inventive apparatus for partitioning a sampling region on a solid surface in a contactless manner.

In addition, as shown in FIG. 15, four lamp-type light sources 131 and four colored filters 141 are used. In this case, as shown in FIG. 17(b), the partitioning portions 142 of the colored filters 141 and 141' include four radially opposite linear partitioning FIGS. 141 and 141' having shapes of "└", "┌", "┘" and "┐" or "\", "/", "/", "\", so that light having passed through each of the colored filters 141 and 141' forms a linearly partitioned sampling region 10 on the solid surface P.

Specifically, when the sampling region 10 is partitioned on the solid surface P using four lamp-type light sources 131 and 131' and four colored filters 141 and 141' as described above, the sampling region having a "☐" or "◯" shape as shown in FIG. 4 or 5 with respect to the sample collection method is partitioned.

Figure 16:
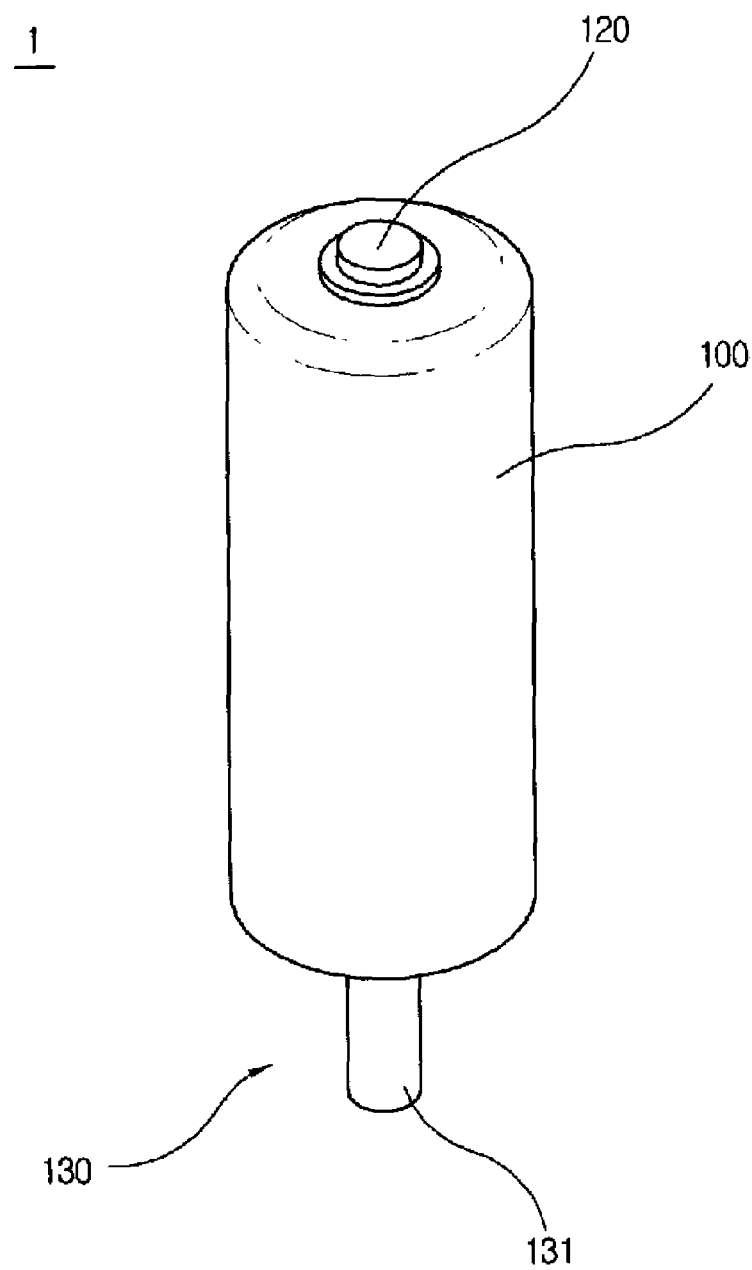
FIG. 16 is a perspective view showing a third embodiment of the inventive apparatus for partitioning a sampling region on a solid surface in a contactless manner.

Moreover, as shown in FIG. 16, one lamp-type light source 131 and one colored filter are used. In this case, as shown in FIG. 17(c), the partitioning portion 142 of the colored filter 141 includes a linear partitioning FIG. 142a having a shape of "☐" or "◯", so that light having passed through the colored filter 141 forms a linearly partitioned sampling region 10 on the solid surface P.

Specifically, when the sampling region 10 is partitioned on the colored filter using one lamp-type light source 131 and one colored filter 141 as described above, the sampling region 10 having a shape of "☐" or "◯" as shown in FIG. 6 or 7 with respect to the sample collection method is partitioned.

Meanwhile, as shown in FIG. 18, the transparent partitioning portions 142 of the colored filters 141 and 141' may include partitioning surfaces 142b and 142b'. In this case, light having passed through the colored filters 141 and 141' forms a surface-shaped partitioning region 10 on the solid surface P.

Specifically, the sampling region 10 is partitioned on the solid surface P using the colored filters 141 and 142 having the partitioning surfaces 142b and 142b' as described above, the sampling region 10 having a shape of "■" or "●" as shown in FIG. 8 with respect to the sample collection method is partitioned.

Figure 19:
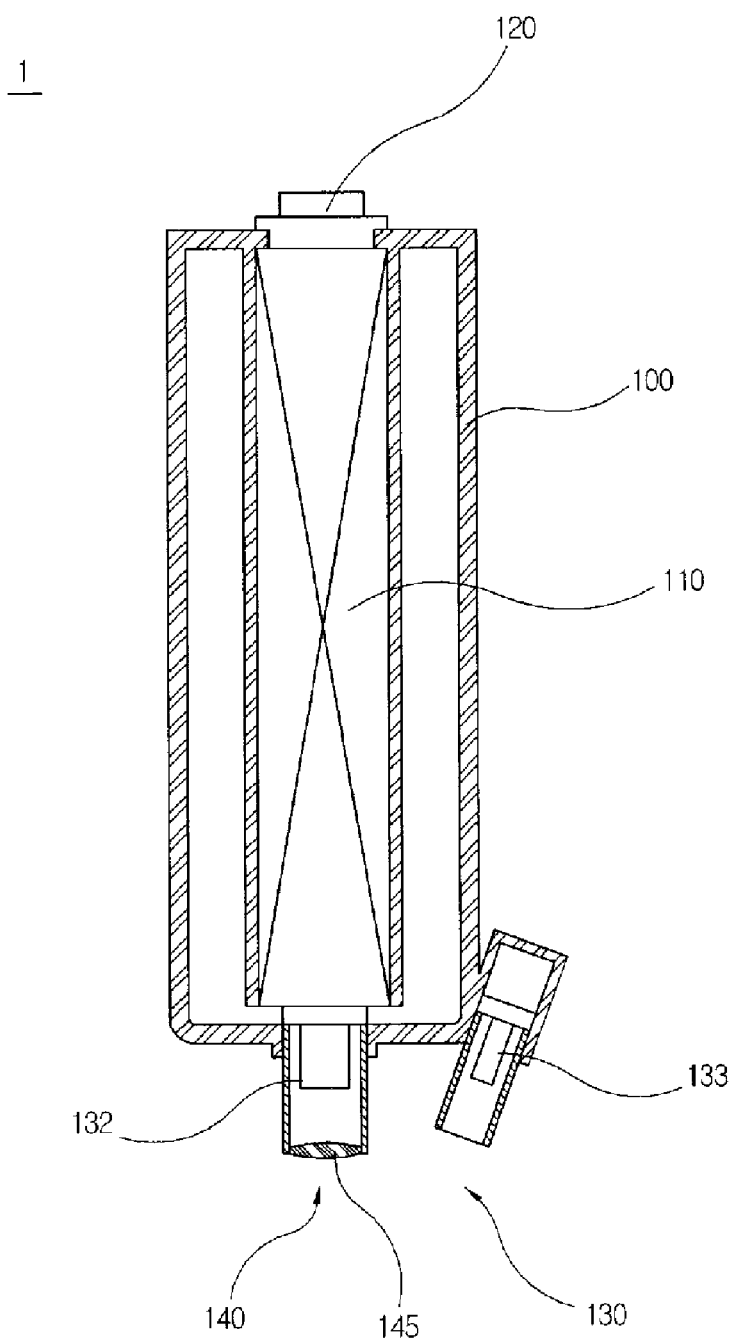
FIG. 19 is a cross-sectional view showing a fourth embodiment of the inventive apparatus for partitioning a sampling region on a solid surface in a contactless manner.
Figure 20:
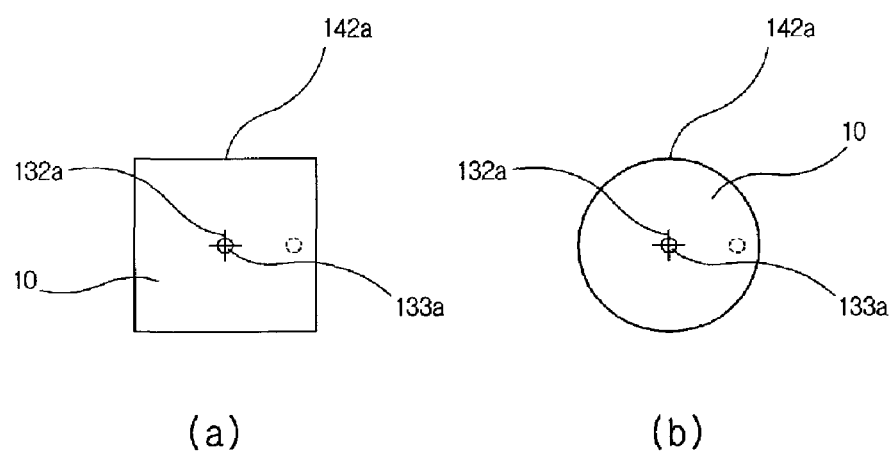
FIG. 20 is a top view showing a sampling region according to a fourth embodiment of the inventive apparatus for partitioning a sampling region on a solid surface in a contactless manner.

In addition, as shown in FIG. 19, the light source 130 of the body 100 of the partitioning apparatus may comprise the laser-type main light source 132 having straightness, and the partitioning means 140 may comprise the diffraction lens 145 having the property of enlarging an image, and the laser-type auxiliary light source 133 having straightness may further be provided at one side of the body 100 of the partitioning apparatus so as to be slanted toward the main light source 132. In this case, the main light source 132 is configured to irradiate light along the partitioning line 142a and the central point 132a of the region partitioned by the partitioning line 142a, and the auxiliary light source 133 is configured to irradiate light onto the auxiliary point 133a that progresses toward the central point 132a. The distance between the body 100 and the solid surface P is controlled so that a figure-shaped sampling region 10 is partitioned on the solid surface P when the central point 312a and the auxiliary point 133a overlap each other as shown in FIG. 20.

Specifically, when the sampling region 10 is to be partitioned on the solid surface P using the main light source 132 and the auxiliary light source 133 as described above, the central point 132a of the main light source 132 overlaps with the auxiliary point 133a of the auxiliary light source 133 as shown in FIG. 9 or 10 with respect to the sample collection method, and thus the sampling region 10 having a shape of "⊡" or "⊙" is partitioned on the solid surface.

Figure 21:
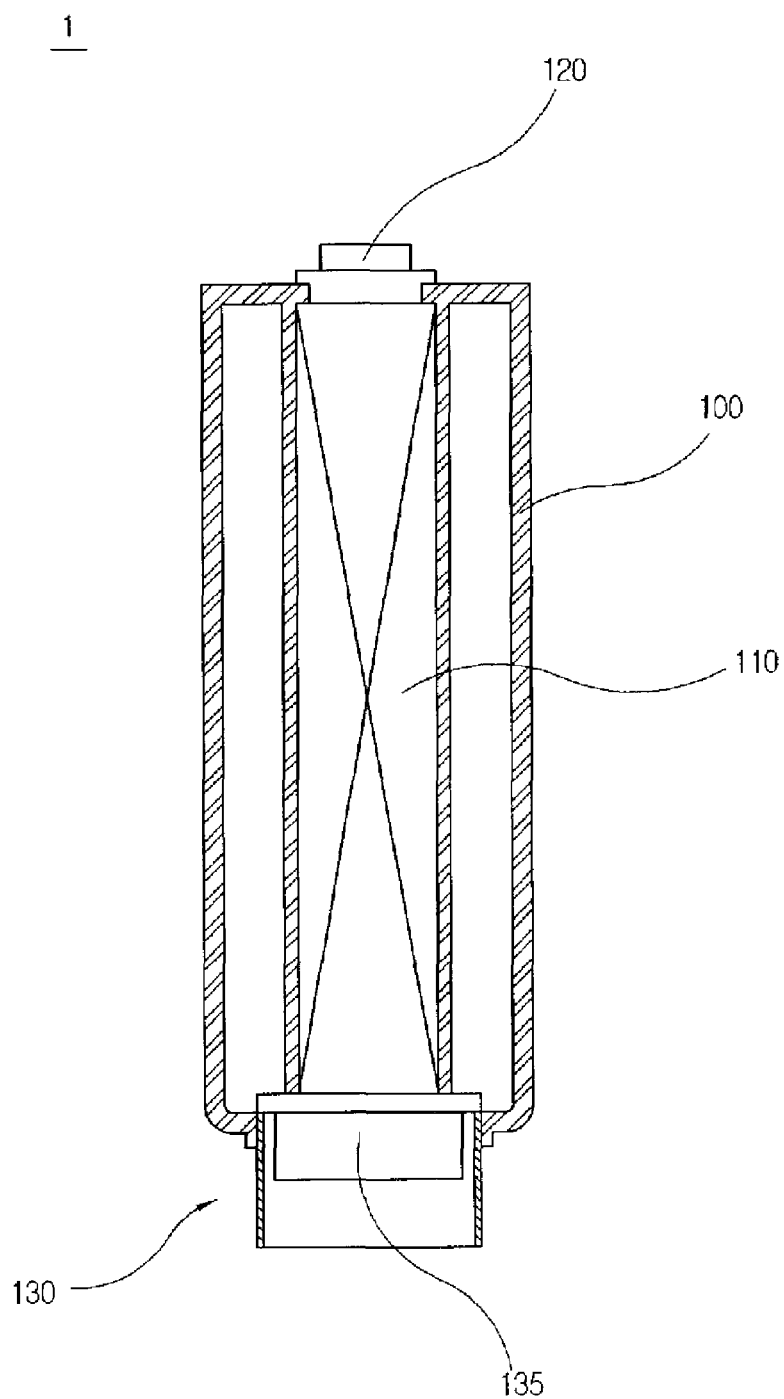
FIG. 21 is a cross-sectional view showing a sampling region according to a fifth embodiment of the inventive apparatus for partitioning a sampling region on a solid surface in a contactless manner.
Figure 22:
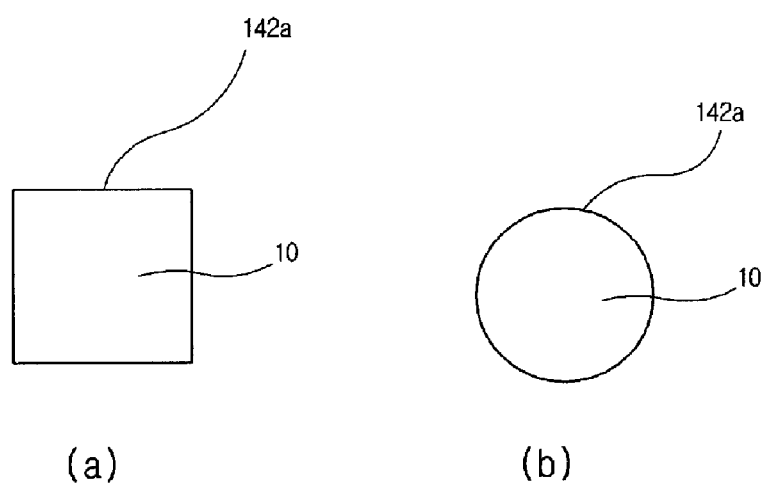
FIG. 22 is a top view showing a sampling region according to a fifth embodiment of the inventive apparatus for partitioning a sampling region on a solid surface in a contactless manner.

In addition, as shown in FIG. 21, the battery 110 for supplying power is provided in the body 100, and the ON/OFF operating switch 120 is provided at the top of the body 100, and a laser-type light source 135 having straightness is provided at the bottom of the body 100, wherein the light source 135 is configured to irradiate light along a partitioning line 142a as shown in FIG. 22 so as to project an image corresponding to the sampling region 10 onto the solid surface 10.

Specifically, when the sampling region 10 is to be partitioned on the solid surface P using the light source 135 as described above, the sampling region 10 having the same size as the partitioning line 142a and a shape of "☐" or "◯" as shown in FIG. 11 or 12 with respect to the sample collection method is partitioned.

Meanwhile, the figure-shaped sampling region 10 projected on the solid surface P by the projection of the light source 130 preferably has an area of 100 cm².

When the above-described method for collecting a microbial sample from the solid surface using a contactless partitioning system and the above-described apparatus for partitioning a sampling region on a solid surface are used, the sampling region can be partitioned in a convenient and rapid manner, and the contamination of the solid surface can be fundamentally prevented, and thus the accuracy of sampling operations such as microbial collection can be further increased.

Furthermore, the apparatus can be reused, and thus the cost of a sampling operation can be significantly reduced.

The invention claimed is:

1. A method for forming a figure-shaped microbial sample collecting region on a solid surface, the method comprising steps of:
   (a) projecting light from two or more projecting light sources through two or more corresponding masks or filters onto the solid surface to create two or more corresponding partial projected images, wherein each mask or filter includes an equal portion of the figure-shaped microbial sample collecting region so that each of the two or more corresponding partial projected images represents an equal portion of the figure-shaped microbial sample collecting region;
   (b) controlling a distance of the two or more projecting light sources from the solid surface;
   (c) collecting microorganisms from the figure-shaped microbial sample collecting region on the solid surface by wiping the sample collecting region with a collection means; and
   (d) preparing a suspension of the microorganisms by mixing and strongly shaking the collection means for collecting microorganisms with sterile physiological saline,
   wherein the controlling step (b) comprises forming the figure-shaped microbial sample collecting region so that when each of the two or more corresponding partial projected images adjoin, the figure-shaped microbial sample collecting region is formed on the solid surface,
   wherein step (c) comprises collecting the microorganisms from the figure-shaped microbial sample collecting region on the solid surface by the collection means selected from a sterile gauze and cotton swab wetted with 1-5 ml of sterile physiological saline, and the step (d) comprises mixing the collection means with 10-100 ml of saline physiological saline to prepare the suspension.

2. A method for forming a figure-shaped microbial sample collecting region on a solid surface, the method comprising steps of:
   (a) projecting light from a projecting light source through a corresponding mask or filter onto the solid surface to create a projected image having a centrally located mark, wherein the projecting light source is a laser-type light source;
   (b) projecting light from an auxiliary light source located at a fixed angle relative to the projecting light source to create a projected dot;
   (c) controlling a distance of the projecting light source and the auxiliary light source from the solid surface so that the figure-shaped microbial sample collecting region is formed when the projected dot is aligned with the centrally located mark;
   (d) collecting microorganisms from the figure-shaped microbial sample collecting sampling region on the solid surface by wiping the sampling region with a collection means; and
   (e) preparing a suspension of the microorganisms by mixing and strongly shaking the collection means for collecting microorganisms with sterile physiological saline.

3. The method of claim 1, wherein figure-shaped microbial sample collecting region has an area of 100 cm$^2$.

* * * * *